US012601544B2

(12) United States Patent
Zechlin et al.

(10) Patent No.: US 12,601,544 B2
(45) Date of Patent: Apr. 14, 2026

(54) DRYING APPARATUS AND USE THEREOF AND PROCESS FOR PRODUCING AN ISOCYANATE USING THE DRYING APPARATUS

(71) Applicants: Covestro Intellectual Property GmbH & Co. KG, Leverkusen (DE); Covestro Deutschland AG, Leverkusen (DE)

(72) Inventors: Joachim Zechlin, Neuss (DE); Alexander Plum, Cologne (DE); Martin Kuhlmann, Cologne (DE)

(73) Assignee: Covestro Deutschland AG, Leverkusen (DE)

( * ) Notice: Subject to any disclaimer, the term of this patent is extended or adjusted under 35 U.S.C. 154(b) by 812 days.

(21) Appl. No.: 17/598,946

(22) PCT Filed: Mar. 31, 2020

(86) PCT No.: PCT/EP2020/059107
§ 371 (c)(1),
(2) Date: Sep. 28, 2021

(87) PCT Pub. No.: WO2020/201277
PCT Pub. Date: Oct. 8, 2020

(65) Prior Publication Data
US 2022/0187018 A1     Jun. 16, 2022

(30) Foreign Application Priority Data

Apr. 2, 2019   (EP) ..................................... 19166805
Mar. 2, 2020   (EP) ..................................... 20160487

(51) Int. Cl.
*F26B 25/00*     (2006.01)
*C07C 263/10*     (2006.01)
*C07C 263/20*     (2006.01)

(52) U.S. Cl.
CPC .......... *F26B 25/006* (2013.01); *C07C 263/10* (2013.01); *C07C 263/20* (2013.01); *F26B 2200/18* (2013.01)

(58) Field of Classification Search
None
See application file for complete search history.

(56) References Cited

U.S. PATENT DOCUMENTS 4,824,257 A     4/1989  List et al.
4,847,408 A     7/1989  Frosch et al.
(Continued)

FOREIGN PATENT DOCUMENTS

CH     706804 A2 *  2/2014  ............. C10B 47/12
CN     1439857 A    9/2003
(Continued)

OTHER PUBLICATIONS

Espacenet English translation of Riemann (DE 4200890 A1).*
(Continued)

*Primary Examiner* — Jason Lau
(74) *Attorney, Agent, or Firm* — Donald R. Palladino

(57) ABSTRACT

The present invention relates to a drying apparatus for evaporating volatile constituents from a starting material to be dried, to a process for producing an isocyanate using this drying apparatus and to the use of the drying apparatus for drying distillation bottoms streams, oil-containing waste, waste paint or coating materials, sewage sludges, mineral substances and coal slurries contaminated with organic compounds. In the drying apparatus the evaporated constituents (vapours) are passed into a condenser via a vapor dome and a vapor conduit. The drying apparatus has the feature that partial condensation of the vapours in the vapor dome and/or in the vapor conduit is intentionally allowed or induced during operation, and condensed constituents of the
(Continued)

vapours are discharged from the drying apparatus via means installed for this purpose in the vapor dome and/or the vapour conduit.

14 Claims, 2 Drawing Sheets

(56)                    References Cited

U.S. PATENT DOCUMENTS

|  |  |  |  |  |
|---|---|---|---|---|
| 5,446,196 | A | 8/1995 | Benedix et al. | |
| 5,609,735 | A | 3/1997 | Hetzel et al. | |
| 6,393,850 | B1 | 5/2002 | Vanderstraeten | |
| 7,108,770 | B2 | 9/2006 | Grun et al. | |
| 7,504,533 | B2 | 3/2009 | Boehm et al. | |
| 8,088,944 | B2 | 1/2012 | Woelfert et al. | |
| 8,495,822 | B2 | 7/2013 | Kim et al. | |
| 9,334,172 | B2 | 5/2016 | Campos et al. | |
| 10,703,713 | B2 | 7/2020 | Loddenkemper et al. | |
| 2003/0230476 | A1 | 12/2003 | Brady et al. | |
| 2016/0265768 | A1* | 9/2016 | Park | F23L 13/02 |
| 2017/0015909 | A1* | 1/2017 | Heimann | B01J 20/20 |
| 2021/0024833 | A1 | 1/2021 | Schlager | |
| 2021/0040397 | A1 | 2/2021 | Fleury et al. | |
| 2021/0363099 | A1 | 11/2021 | Ryu et al. | |

FOREIGN PATENT DOCUMENTS

| | | | |
|---|---|---|---|
| CN | 201155907 | Y | 11/2008 |
| CN | 201912935 | U | 8/2011 |
| CN | 202199136 | U | 4/2012 |
| CN | 102743893 | A | 10/2012 |
| CN | 102872611 | A | 1/2013 |
| CN | 202860138 | U | 4/2013 |
| CN | 103804236 | A | 5/2014 |
| CN | 203790820 | U | 8/2014 |
| CN | 106153430 | A | 11/2016 |
| CN | 205815162 | U | 12/2016 |
| CN | 107477999 | A | 12/2017 |
| CN | 206823214 | U | 1/2018 |
| CN | 207797516 | U | 8/2018 |
| CN | 208059415 | U | 11/2018 |
| CN | 208635444 | U | 3/2019 |
| CN | 109631561 | A | 4/2019 |
| CN | 208809498 | U | 5/2019 |
| CN | 210495821 | U | 5/2020 |
| CN | 211612704 | U | 10/2020 |
| DE | 3912586 | A1 | 11/1989 |
| DE | 4200890 | A1 * | 7/1993 ............... B09C 1/06 |
| DE | 102012108261 | B4 | 8/2017 |
| EP | 2540702 | A2 | 1/2013 |
| WO | 2012159736 | A1 | 11/2012 |

OTHER PUBLICATIONS

English translation of col. 6, lines 31-51 of Riemann.*
Chem System's PERP Report for TDI/MDI (Chem Systems, Process Evaluation Research Planning 30 TDI/MDI 98/99 S8, Tarrytown, N.Y., USA: Chem Systems, Oct. 1999, pp. 27 to 32).
International Search Report Application No. PCT/EP2020/059107, mailed Jun. 2, 2020, 4 pages.

* cited by examiner

DRYING APPARATUS AND USE THEREOF AND PROCESS FOR PRODUCING AN ISOCYANATE USING THE DRYING APPARATUS

CROSS-REFERENCE TO RELATED APPLICATION

This application is a national stage application under 35 U.S.C. § 371 of PCT/EP2020/059107,filed Mar. 31, 2020, which claims the benefit of European Application No. 19166805.2, filed Apr. 2, 2019 and European Application No. 20160487.3, filed Mar. 2, 2020, each of which is incorporated herein by reference.

FIELD

The present invention relates to a drying apparatus for evaporating volatile constituents from a starting material to be dried, to a process for producing an isocyanate using this drying apparatus and to the use of the drying apparatus for drying distillation bottoms streams, oil-containing wastes, paint or coatings wastes, sewage sludges, mineral materials contaminated with organic compounds and coal slurries. In the drying apparatus the evaporated constituents (vapors) are passed via a vapor dome and a vapor conduit into a condenser. The drying apparatus has the feature that in operation thereof partial condensation of the vapors in the vapor dome and/or in the vapor conduit is intentionally permitted or induced and condensed constituents of the vapors are discharged from the drying apparatus via means installed for this purpose in the vapor dome and/or the vapor conduit.

BACKGROUND

Many fields of technology employ apparatuses used for removing volatile constituents from a (generally already very viscous but still flowable) starting material by evaporation to obtain a ("dried") material depleted of the volatile constituents which is generated as a solid or high viscosity liquid. Such apparatuses are typically referred to as dryers or drying reactors even if they are by no means always used for "drying" in the sense of dewatering. Known dryer types include product-turning vacuum dryers having a horizontal shaft (see for example EP 0 626 368 A1), rotary dryers, disc dryers (see for example EP 0 289 647 A1), belt dryers, granulating screws and fluidized bed dryers (see for example WO 2012/159736 A1).

Thus, many branches of industry generate distillation bottoms streams, for example, which contain not only the high-boiling constituents of the starting mixture of the distillation but also a certain proportion of more volatile components which have often intentionally been incompletely distilled off in order to keep the distillation bottoms stream flowable even at moderate temperature as necessitated by a continuous distillation.

Examples may be found in the production of isocyanates by phosgenation and in the manufacture of their precursor compounds, the corresponding primary amines. Specific examples include distillation bottoms streams formed in the production of tolylene diisocyanate (TDI) and the amine precursor thereof tolylenediamine (TDA). In both cases such distillation bottoms streams contain not only high-boiling secondary components (often referred to as distillation residue or residue for short) but regularly also considerable proportions of value product (TDI/TDA). Examples include the patent applications DE 10 2012 108 261 A1 (kneader dryer), EP 2 540 702 A2 (fluidized bed dryer) and WO 2018/114846 A1 (various dryer types) which are concerned with the workup of TDI residues. One example of the use of a product-turning vacuum dryer having a horizontal screw is European patent application EP 0 626 368 A1. This application relates to a process for producing pure, distilled isocyanates by reacting the corresponding amines with phosgene in a suitable solvent and multi-stage, distillative workup into pure isocyanates, pure solvent and a proportion of residue, this residue being subjected to continuous workup. The workup is characterized in that the residue obtained from the distillation process is continuously supplied to a heated, product-turning vacuum dryer having a horizontal shaft together with 2% to 50% by weight of high-boiling hydrocarbons, preferably bitumen, inert under the distillation conditions, the proportion of isocyanates still present in the residue is continuously distilled off at temperatures of 160° C. to 280° C. and pressures of 2 to 50 mbar and the remaining residue is continuously discharged as free-flowing, non-dusting granulate material, optionally cooled and optionally sent for incineration after milling. In the example a liquid mixture of 67.4% by weight of meta-TDI, 29.1% by weight of polymeric residue and 3.5% by weight of solvent is supplied from above at three points to a dryer of the described type heated to an internal temperature of 240° C. and evacuated to a pressure of 12 mbar. At the end of the dryer opposite the feed points dried granulate is discharged at the bottom via a rotary feeder while a mixture of TDI and solvent is discharged at the top at two points. An intentional partial condensation of vapors in a vapor dome and/or a vapor conduit is not disclosed in this patent application. It is mentioned merely as a type of secondary aspect that condensate generated in the attached vapor system is discharged separately for removal of any dust deposits on the walls thereof. It is not apparent therefrom at which point in the vapor system and under what conditions condensate is generated (or whether condensate is regularly generated at all).

Residues also remain in the refining of crude oil after removal of the distillable crude oil fractions used for production of valuable substances such as heating gas, auto gas (LPG), auto fuels, solvents and kerosene. Such residues may for example be passed into a coker plant and "cracked", i.e. chemically broken down into substances of lower molar mass at high temperatures (for example 500° C.). As an alternative, German patent application DE 10 2017 103 363 A1 (also published as WO 2018/149951A1) proposes subjecting such residues to a vacuum at a pressure of 10 mbar or less and to a temperature of at least 300° C. in a kneader dryer (also referred to as a kneader-mixer or kneader reactor) in order to separate the volatile constituents (comprising valuable products) not removable by the preceding distillation steps via a vapor conduit and to discharge the remaining non-volatile substances via a discharging apparatus. International patent application WO 2016/078994 A1 is also concerned with the workup of refining residues using kneader-mixers.

Drying apparatuses as described at the outset are likewise employed in the workup of waste products such as oil-containing wastes, paint or coatings wastes and sewage sludges. The same applies to the dewatering of coal slurries obtained for example through hydrothermal carbonization of biomass. German patent application DE OS 39 12 586 describes a process and a regeneration means for thermal treatment such as for example drying, carbonization or gasification of pasty or sludge-like substances (for example pit-moist coal) in a heated reactor such as for example a fluidized bed reactor. The medium exiting the reactor as a gas phase comprises condensable vapors which are condensed, thus making the medium reusable and recycling it to the reactor via a recirculation blower (3, cf. figure). A recuperative heat exchanger (4) which is configured as a deheater/reheater is connected upstream of two condensers (2) arranged in series so that these are supplied with saturated medium and the recirculating blower (3) has dry medium flowing through it. The heat exchanger (4) thus effects a cooling of the gas phase exiting the reactor by heat exchange with the cold vapors exiting the condensers (without material contact of the gas phase with the cold vapors; also referred to as indirect heat exchange) which are thus quasi-superheated and can thus be recycled to the reactor without the risk of droplet formation. Any liquid proportions formed during this cooling of the gas phase exiting the reactor are supplied to the condensers together with the gaseous remaining proportions and not discharged via a drainage means. An intentional partial condensation of vapors in a vapor dome and/or a vapor conduit to avoid deposits is not disclosed in this patent application.

A further application for such apparatuses is the thermal treatment of organics-contaminated mineral materials, in particular of soil contaminated in this way, to expel the contaminating substances. A corresponding process is described in German patent application DE 42 00 890 A1. A drying unit is described (see FIG. 3) and the dryer itself is in the form of a disk dryer. The dryer is supplied with the necessary thermal energy via a thermal oil system (10). The individual chemical products and the steam exit the dryer (3) via a vapor dome and from there via a conduit (33) and are supplied to a plurality of serially connected precipitation apparatuses (27). These precipitation apparatuses consist of condensers (28, 29) and heated collection vessels (30, 31), wherein the last condenser (29) has a vacuum unit (32) connected to it. Arranged between the condensers 28 and 29 are another steam generator (35) and a hot water generator (36) in which a cooling of the vapors will naturally also occur. An intentional partial condensation of vapors in the vapor dome and/or the vapor conduit between the vapor dome and the first condenser (28) in the flow direction is not disclosed in this patent application.

In the prior art it is typical to endeavor to discharge the evaporated volatile constituents (vapors) of the starting mixture to be dried from the dryer ideally without recondensation, since backflow for instance of constituents condensed on relatively cold surfaces into the composition to be dried is undesirable. The formation of solid deposits on such relatively cold surfaces would also be a concern. Therefore, it is customary for all surfaces that may come into contact with the generated vapors (in particular a vapor dome arranged on the actual drying space and the discharge conduit for the vapors) to be at least well insulated and often even trace-heated. This is also the case in the abovementioned German patent application DE 42 00 890 A1, where it is expressly stated in column 6, lines 47 to 51 that "volatile constituents exiting the drying unit, i.e. the dryer (3) are passed to the relevant precipitation apparatuses (27) . . . in a <u>heated</u> pipeline system, i.e. conduit (33)".

However, operational practice has shown that the insulation or even heating of these means does not always have the desired effect and that formation of deposits may neverthe-less occur which in extreme cases may even have the result that the drying operation must be regularly interrupted and the apparatuses repeatedly cleaned. There was therefore a need for further improvements in this field of technology.

SUMMARY

In order to meet the abovementioned need the present invention provides a drying apparatus (1000) configured for (continuous) performance of a drying operation of a starting material (10) to be dried to obtain a dried material (20) and a vapor phase (30, =vapors) comprising:

a dryer (100) comprising a heatable drying space (110) having (at least) one feed opening (120) for the starting material (10), (at least) one discharge opening (130) for the dried material (20) and (at least) one passage (140) for the vapor phase (30), wherein the passage opens into (at least) one vapor dome (150) comprising a discharge opening (160) for the vapor phase;

(at least) one condenser connected downstream of the discharge opening for the vapor phase;

a vapor conduit (200) connecting the discharge opening (160) for the vapor phase (30) with the condenser (300);

wherein (i) the vapor dome (150), but not the vapor conduit (200), is configured such that in it (i.e. in the vapor dome (150)) a partial condensation of the vapor phase during the drying operation is (continuously) effected or (ii) the vapor conduit (200), but not the vapor dome (150), is configured such that in it (i.e. in the vapor conduit (200)) a partial condensation of the vapor phase during the drying operation is (continuously) effected or (iii) the vapor dome (150) and the vapor conduit (200) are configured such that in these (i.e. in the vapor dome (150) and in the vapor conduit (200)) a partial condensation of the vapor phase is (continuously) effected during the drying operation, wherein a drainage means (151, 201) for constituents (31, 32) of the vapor phase (30) liquefied in the partial condensation is arranged in case (i) inside the vapor dome (150), in case (ii) inside the vapor conduit (200), and in case (iii) inside the vapor dome (150) and inside the vapor conduit (200), wherein the drainage means is configured such that the constituents (31, 32) liquefied in the partial condensation are discharged via a discharge opening (152, 202)

from the vapor dome (in case (i)), from the vapor conduit (in case (ii)), or from the vapor dome and from the vapor conduit (in case (iii)), and are thus separated from constituents of the vapor phase not liquefied in the partial condensation (the constituents liquefied in the partial condensation (31, 32) are thus discharged from the drying apparatus (1000) and not for instance recycled into the drying space (110)).

The invention further provides a process for producing an isocyanate by phosgenation of the primary amine corresponding to the isocyanate to be produced to obtain a liquid crude process product comprising the isocyanate to be produced, comprising the distillative workup of this liquid crude process product to obtain a distillation bottoms stream;

further comprising the workup of this distillation bottoms stream, wherein this workup comprises the steps of:

1) optional preconcentration of the distillation bottoms stream in an evaporator by partial evaporation of the isocyanate to be produced present in the distillation bottoms stream, wherein a preconcentrated liquid stream depleted in isocyanate to be produced is obtained;

2) drying the distillation bottoms stream or the preconcentrated liquid stream depleted in isocyanate to be produced obtained in step 1) in the drying apparatus according to the invention, wherein, while forming a solid process product as dried material, isocyanate to be produced is obtained as a vapor phase and liquefied in the condenser.

The invention further provides for the use of the drying apparatus according to the invention for drying starting materials selected from the group consisting of distillation bottoms streams, oil-containing wastes, paint or coatings wastes, sewage sludges, coal slurries and mineral materials contaminated with organic compounds (in particular correspondingly contaminated soil), preferably selected from the group consisting of distillation bottoms streams, oil-containing wastes, paint or coatings wastes, sewage sludges and coal slurries.

BRIEF DESCRIPTION OF THE DRAWINGS

Various features and characteristics of the inventions described in this specification may be better understood by reference to the accompanying figures, in which.

DETAILED DESCRIPTION

In the context of the present invention a vapor dome is to be understood as meaning a dome arranged on the dryer in which vapor phase ascending from the drying space (=ascending vapors) collects. The term vapor conduit describes the conduit through which the vapor phase (=the vapors) flows from the vapor dome into the condenser. If a plurality of condensers (for example 2 to 4 or precisely 2) are connected in series the term vapor conduit is in the terminology of the present invention to be understood as meaning the conduit which connects the vapor dome with the first condenser in the flow direction of the vapor phase (=the vapors).

Drainage means are to be understood as meaning internals or pipeline low points for collecting descending condensate which are configured for predominantly to completely collecting and intentionally discharging from the vapor dome/from the vapor conduit descending condensate condensing on the inner walls of the vapor dome and/or the vapor conduit.

It has quite surprisingly been found that, in contrast to the prevailing view in the prior art to date, a (partial) condensation of the vapor phase formed in the dryer in the vapor dome and/or in the vapor conduit is not only not disadvantageous but can in fact be advantageous since condensate descending down the inner walls of the vapor dome/vapor conduit reduces the tendency for formation of deposits and any deposits that are formed can be continuously washed away. It has thus quite surprisingly been found that the insulation or even heating of the vapor dome and the vapor conduit generally considered essential in the prior art may in fact be the cause of the formation of deposits. The present invention is therefore characterized by an intentional partial condensation of the vapor phase in the vapor dome and/or in the vapor conduit which occurs during the entire drying operation, i.e. continuously (and not only in particular operating states deviating from normal operation for instance). Backflow into the composition to be dried is very largely to completely prevented by the drain means provided according to the invention.

In the attached figures

Figure 1:
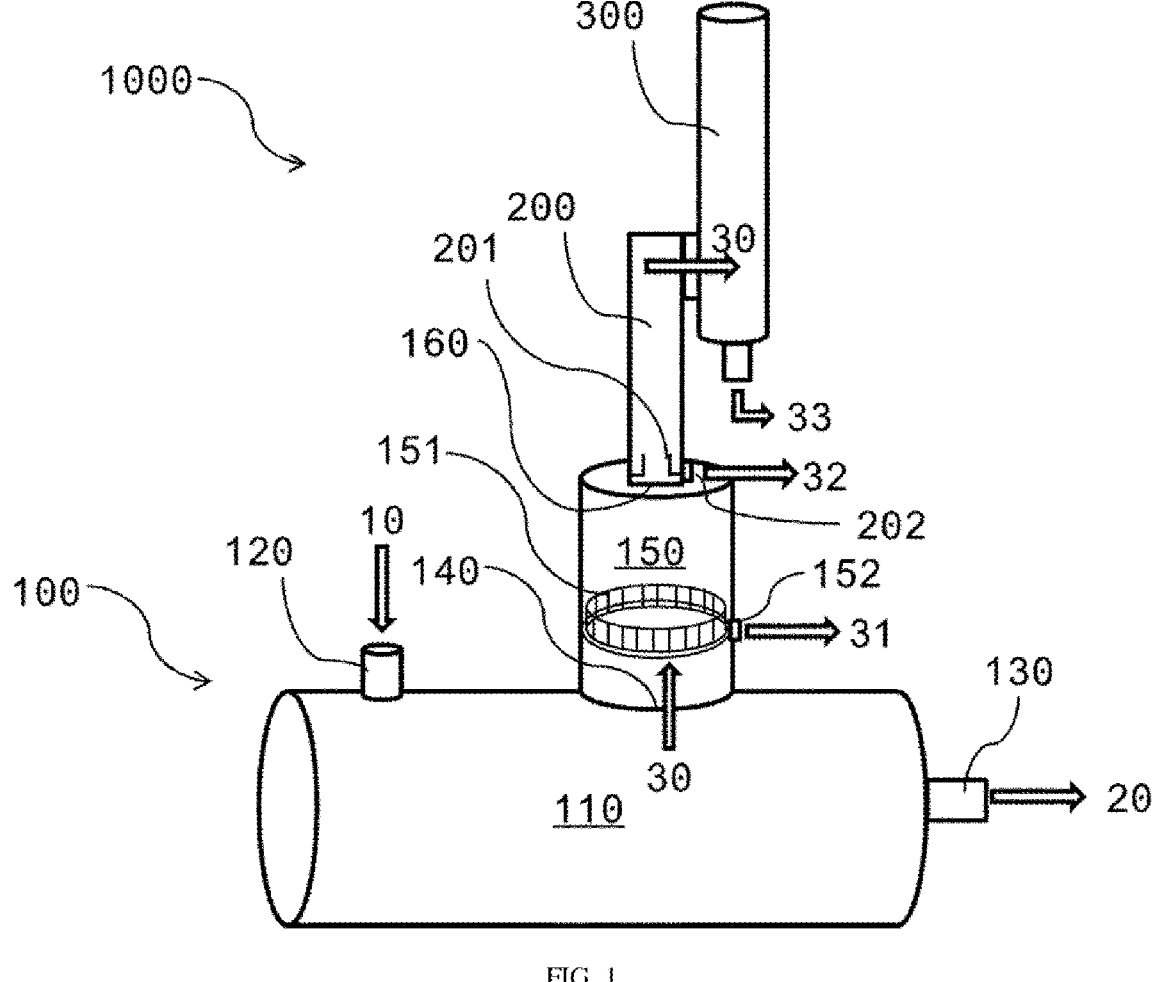
FIG. 1 shows a possible configuration of the drying apparatus according to the invention (1000)
Figure 2:
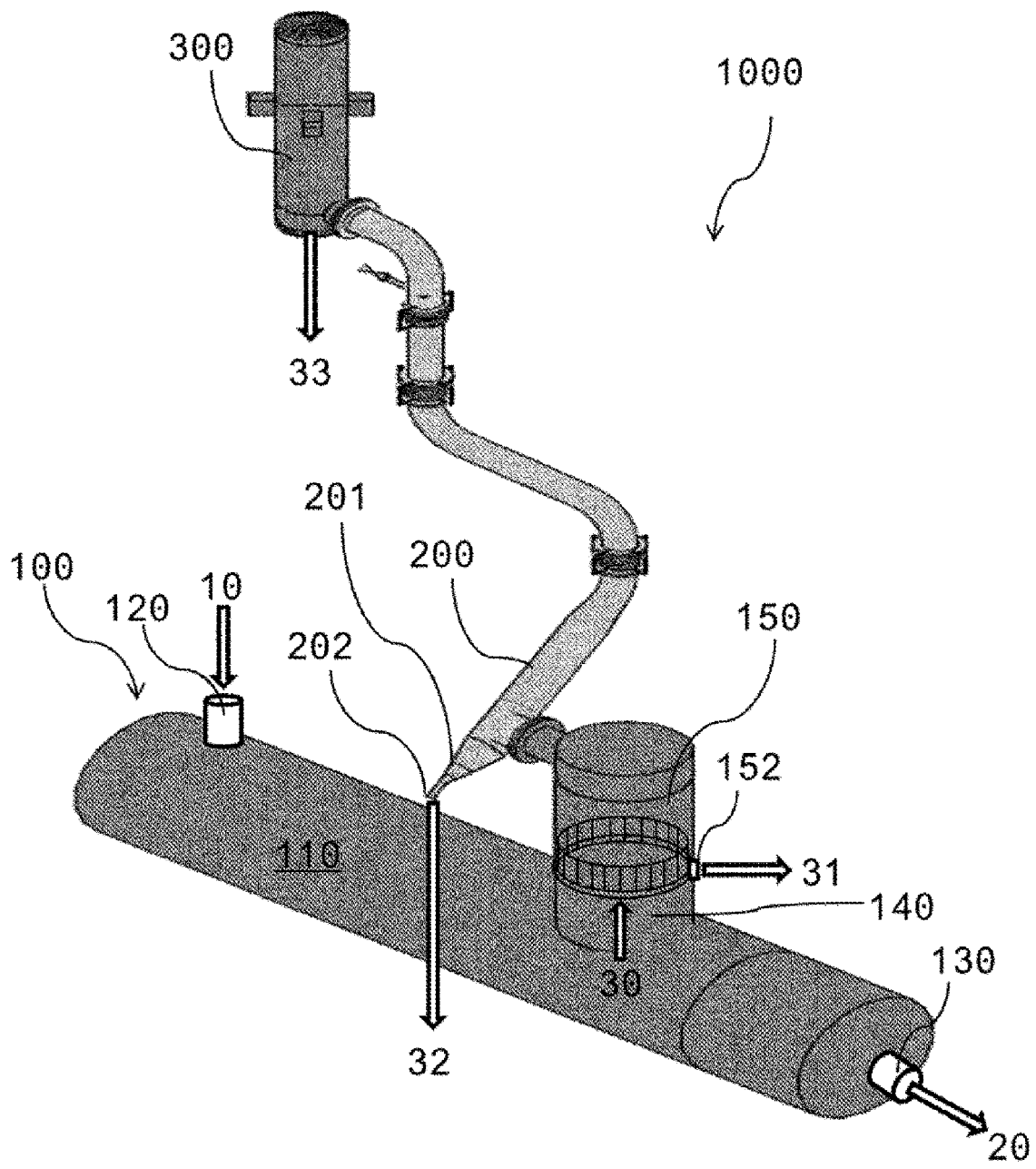
FIG. 2 shows a further possible configuration of the drying apparatus according to the invention (1000).

FIG. 1 shows a possible configuration of the drying apparatus according to the invention (1000);

FIG. 2 shows a further possible configuration of the drying apparatus according to the invention (1000).

The reference numerals have the same definitions in both figures.

Initially specified below is a brief summary of various possible embodiments.

In a first embodiment of the drying apparatus according to the invention, which can be combined with all other embodiments, the dryer is selected from the group consisting of product-turning vacuum dryers having a horizontal screw, rotary dryers, disc dryers, belt dryers and granulating screws.

In a second embodiment of the drying apparatus according to the invention, which is a particular configuration of the first embodiment, the dryer is a product-turning vacuum dryer selected from the group consisting of kneader dryers, paddle dryers and shovel dryers.

In a third embodiment of the drying apparatus according to the invention, which is a particular configuration of the second embodiment, the dryer is a shovel dryer having an interior in which is arranged a rotor shaft rotatably propellable about its axis and configured to distribute for distributing the starting material over a solid material fluidized by means of rotor blades arranged on the rotor shaft during the drying operation and conveying it from the feed opening in the direction of the discharge opening, wherein the solid material is dried material or an inert solid.

In a fourth embodiment of the drying apparatus according to the invention, which can be combined with all other embodiments, the partial condensation of the vapor phase is realized by not having insulation of the vapor dome and/or of the vapor conduit.

In a fifth embodiment of the drying apparatus according to the invention, which can be combined with all other embodiments, the partial condensation of the vapor phase is realized by not having a system to heat the vapor dome and/or of the vapor conduit.

In a sixth embodiment of the drying apparatus according to the invention, which can be combined with all other embodiments, the partial condensation of the vapor phase is realized by a means for cooling the vapor dome and/or the vapor conduit.

In a seventh embodiment of the drying apparatus according to the invention, which can be combined with all other embodiments, the vapor dome comprises a drainage means, where said drainage means is selected from the group consisting of drainage channels (also known as drainage collars) connected to a drainage conduit and droplet collectors connected to a drainage conduit.

In an eighth embodiment of the drying apparatus according to the invention, which can be combined with all other embodiments, the vapor conduit comprises a drainage means, where said drainage means is selected from the group consisting of a drainage funnel connected to a drainage conduit, low points in the vapor conduit connected to a drainage conduit and drainage channels in the vapor conduit connected to a drainage conduit.

In a ninth embodiment of the drying apparatus according to the invention, which can be combined with all other embodiments, the condenser is selected from the group consisting of a tube bundle heat exchanger, a plate heat exchanger and a spray condenser.

In a first embodiment of the process according to the invention for producing an isocyanate, which can be combined with all other embodiments provided they do not relate exclusively to a gas phase phosgenation, the phosgenation is performed in the liquid phase in the presence of a solvent.

In a second embodiment of the process according to the invention for producing an isocyanate, which can be combined with all other embodiments provided they do not relate exclusively to a liquid phase phosgenation, the phosgenation is performed in the gas phase to generate a gaseous process product containing the isocyanate to be produced and wherein this gaseous process product is cooled by contacting with a quenching liquid selected from the group consisting of solvent, the isocyanate to be produced and mixtures of the isocyanate to be produced and solvent, thus affording the liquid crude process product comprising the isocyanate to be produced.

In a third embodiment of the process according to the invention for producing an isocyanate, which is a particular configuration of the second embodiment, the quenching liquid is selected from the group consisting of solvent and mixtures of the isocyanate to be produced and solvent.

In a fourth embodiment of the process according to the invention for producing an isocyanate, which is a particular configuration of the first and third embodiment, the solvent is selected from the group consisting of chlorobenzene, ortho-dichlorobenzene, para-dichlorobenzene, the isomers of trichlorobenzene, toluene, the isomers of xylene and mixtures of the abovementioned solvents.

In a fifth embodiment of the process according to the invention for producing an isocyanate, which can be combined with all other embodiments, the drying in step 2) is performed at a temperature in the range from 150° C. to 500° C. and at a pressure in the range from 20 $mbar_{(abs.)}$ to 200 $mbar_{(abs.)}$, preferably at a temperature in the range from 185° C. to 320° C. and at a pressure in the range from 50 $mbar_{(abs.)}$ to 180 $mbar_{(abs.)}$, particularly preferably at a temperature in the range from 250° C. to 310° C. and at a pressure in the range from 80 $mbar_{(abs.)}$ to 150 $mbar_{(abs.)}$.

A sixth embodiment of the process according to the invention for producing an isocyanate, which can be combined with all other embodiments, comprises step 1), wherein the preconcentration is performed at a temperature in the range from 120° C. to 180° C. and at a pressure in the range from 10 $mbar_{(abs.)}$ to 60 $mbar_{(abs.)}$, preferably at a temperature in the range from 130° C. to 175° C. and at a pressure in the range from 25 $mbar_{(abs.)}$ to 45 $mbar_{(abs.)}$.

In a seventh embodiment of the process according to the invention for producing an isocyanate, which can be combined with all other embodiments, the isocyanate to be produced is selected from the group consisting of tolylene diisocyanate, naphthyl diisocyanate, 1,5-pentane diisocyanate, 1,6-hexamethylene diisocyanate, isophorone diisocyanate, xylylene diisocyanate and diisocyanatodicyclohexylmethane.

In an eighth embodiment of the process according to the invention for producing an isocyanate, which is a particular configuration of the seventh embodiment, the isocyanate to be produced is tolylene diisocyanate.

In a first embodiment of the use according to the invention of the drying apparatus according to the invention the use relates to the drying of distillation bottoms streams, wherein the distillation bottoms are generated in the production of isocyanates or in the production of primary amines which may be converted into isocyanates.

In a second embodiment of the use according to the invention of the drying apparatus according to the invention the use relates to the drying of distillation bottoms streams, wherein the distillation bottoms streams are generated in the refining of crude oil.

The embodiments briefly outlined above and further possible configurations of the invention will now be described in more detail below. In this regard, the embodiments may be combined with each other in any manner unless the context indicates otherwise.

Suitable dryers (100) according to the invention are types known to those skilled in the art such as in particular product-turning vacuum dryers (in particular kneader dryers, paddle dryers and shovel dryers) having a horizontal shaft, rotary dryers, disc dryers, belt dryers and granulating screws. Particularly preferred are shovel dryers where previously dried material (or other inert solids particles) is set into motion by a particularly rapidly rotating shovel system which at least approximates a fluidized bed (or ideally and preferably constitutes a fluidized bed) and the starting material to be dried is conveyed onto this quasi-fluidized bed (or actual fluidized bed). The starting material to be dried is thus applied to an at least rudimentarily (ideally and preferably actually) fluidized bed. Such dryers, which are particularly suitable for drying tacky products, have become known by the term combi-fluidization technology (CFT) dryers. In contrast to convective fluidized bed dryers the fluidization effected therein is purely mechanical. CFT dryers are described for example in WO 2012/159736 A1 and EP 2 540 702 A2. These dryers have the feature that they have arranged in the interior of the dryer a rotor shaft rotatably propellable about its axis (not shown in the figures) and are configured to distribute the starting material over a solid material fluidized by means of rotor blades arranged on the rotor shaft during the drying operation and conveying it from the feed opening in the direction of the discharge opening, wherein the solid material is dried material or an inert solid. As mentioned hereinabove it is provided that in operation of these dryers a bed of fluidized material is already present when starting material to be dried is introduced into the dryer for the first time. To this end previously dried material (from an earlier drying operation) or a solid inert under the prevailing conditions (preferably inorganic spherical particles such as in particular spheres of aluminum oxide) are introduced into the dryer and set into motion with the rotor shaft. A startup phase is followed by establishment of a steady operating state in which the starting material is consolidated by drying and partially discharged as solid and partially available for the further drying operation as a fluidized bed of solid particles. A further addition of previously dried material from another drying operation or of inert solid is then of course no longer necessary. The calming zone between the fluidized bed zone and the dry material discharge described in WO 2012/159736 A1 (in the terminology of the present invention the discharge opening (130) for the dried material (20)) may also be used in the context of the present invention.

The drying space (110) is preferably in the shape of a horizontally arranged (substantially) cylindrical body as shown in FIG. 1. Internals arranged in the interior of the drying space (110) for conveying the material to be dried from the feed opening (120) to the discharge opening (130) have been omitted from FIG. 1 (and from FIG. 2) for the sake of simplicity. Such means (such as for example the abovementioned rotor shafts or other means as specified in the literature recited at the outset) are well known to those skilled in the art and discussion thereof at this point can therefore be omitted. The vapor dome (150) is preferably in the shape of a vertically arranged (substantially) cylindrical body. In the prior art the vapor dome is used for gravity separation of any entrained droplets. This is achieved when the cross section of the vapor dome is chosen to be sufficiently large with regard to the other dimensions of the dryer and the type of the material to be dried which is a routine configuration for a person skilled in the art. The vapor dome also fulfills this function in the context of the present invention. However, the partial condensation of the vapor phase according to the invention goes beyond this since a portion of the evaporated constituents of the starting material to be dried is re-liquefied on the inner surface of the vapor dome. The dryer preferably has (precisely) one vapor dome. However, embodiments having more than one vapor dome (in particular 2) are also conceivable.

The dryer according to the invention (100) is continuously operated, by preference at a temperature in the range from 150° C. to 500° C. and at a pressure in the range from 20 mbar$_{(abs.)}$ to 200 mbar$_{(abs.)}$, preferably at a temperature in the range from 185° C. to 320° C. and at a pressure in the range from 50 mbar$_{(abs.)}$ to 180 mbar$_{(abs.)}$, particularly preferably at a temperature in the range from 250° C. to 310° C. and at a pressure in the range from 80 mbar$_{(abs.)}$ to 150 mbar$_{(abs.)}$. It is especially preferable to operate the dryer (100) in such a way that the dried material is generated as a solid.

Depending on the boundary conditions (type of starting material to be dried, operating conditions etc.) a partial condensation of the vapor phase in the context of the invention may already be realized by not having insulation of the vapor dome/the vapor conduit. The vapor dome/the vapor conduit are preferably not heated. Depending on the boiling point of the volatile constituents it may also be necessary to actively cool the vapor dome/the vapor conduit. This may be done in a manner known per se to those skilled in the art, in particular by passing a medium that is colder than the boiling temperature of the vapor phase through cooling jackets or applied cooling coils.

In the abovementioned cases (i) and (iii) a drainage means (151) is present in the vapor dome (150). Preferred drainage means (151) are horizontally circumferential, angled or helically downcast drainage channels (also known as drainage collars) mounted to the inner wall of the vapor dome and connected to a drainage conduit and droplet collectors connected to a drainage conduit (the drainage conduits are not shown in the figures). Such means are known per se to those skilled in the art. The drainage channels preferably cover 75% to 100%, particularly preferably 90% to 100%, very particularly preferably 100%, of the inner vapor dome circumference and preferably have a height of 1 cm to 50 cm and a depth of 1 cm to 50 cm, particularly preferably a height of 10 cm to 30 cm and a depth of 10 cm to 30 cm.

In the abovementioned cases (ii) and (iii) a drainage means (201) is present in the vapor conduit (200). Preferred drainage means (201) are drainage funnels in pipeline low points connected to a drainage conduit, low points in the vapor conduit connected to a drainage conduit and horizontally circumferential, angled or helically downcast drainage channels mounted to the inner wall of the vapor dome and connected to a drainage conduit (the drainage conduits are not shown in the figures). FIG. 2 shows for example an embodiment having a drainage funnel (201) in a low point of the vapor conduit (200). The drainage channels preferably cover 75% to 100%, particularly preferably 90% to 100%, very particularly preferably 100%, of the conduit circumference and have a height of 1 cm to 50 cm and a depth of 1 cm to 20 cm, preferably a height of 10 cm to 30 cm and a depth of 5 cm to 15 cm.

The uncondensed constituents of the vapor phase (30) flow into the condenser (300) where they are liquefied and discharged as stream 33 from the drying apparatus (1000). In the apparatus according to the invention two to three streams of liquefied vapor phase are thus generated, in case (i) stream 31 and stream 33, in case (ii) stream 32 and stream 33 and in case (iii), which is shown in FIG. 1 and particularly preferred, streams 31, 32 and 33. Suitable condensers (300) include means known to those skilled in the art such as in particular tube bundle heat exchangers, plate heat exchangers and spray condensers. It is possible to connect a plurality of condensers in series, in particular 2 to 4 condensers, preferably (precisely) 2 condensers. However, the use of a single condenser is sufficient in many cases and therefore also the most preferred embodiment.

The drying apparatus according to the invention is particularly advantageously employable in the workup of isocyanates, preferably in the workup of tolylene diisocyanate, naphthyl diisocyanate, 1,5-pentane diisocyanate, 1,6-hexamethylene diisocyanate, isophorone diisocyanate, xylylene diisocyanate or diisocyanatodicyclohexylmethane, particularly preferably of tolylene diisocyanate. The present invention thus further provides a process for producing an isocyanate, in particular TDI, by a) phosgenation of the primary amine corresponding to the isocyanate to be produced, i.e. in particular TDA, to obtain a liquid crude process product comprising the isocyanate to be produced, comprising b) the distillative workup of this liquid crude process product to obtain a distillation bottoms stream;

further comprising c) the workup of this distillation bottoms stream, wherein this workup comprises the steps of:

1) optional preconcentration of the distillation bottoms stream in an evaporator by partial evaporation of the isocyanate to be produced present in the distillation bottoms stream, wherein a preconcentrated liquid stream depleted in isocyanate to be produced is obtained;

2) drying the distillation bottoms stream or the preconcentrated liquid stream depleted in isocyanate to be produced obtained in step 1) in a drying apparatus as claimed in any of the preceding claims, wherein, while forming a solid process product as dried material, isocyanate to be produced is obtained as a vapor phase and liquefied in the condenser.

The phosgenation in step a) may be performed in the liquid phase in the presence of a solvent or in the gas phase. When performing the reaction in the gas phase the initially generated gaseous process product containing the isocyanate to be produced is initially cooled by contacting with a quenching liquid to obtain a liquid crude process product comprising the isocyanate to be produced. Suitable quenching liquids include in particular organic solvents, the isocyanate to be produced itself or mixtures of the isocyanate to be produced and organic solvents. The quenching liquid usually contains organic solvents. Suitable solvents for this purpose (as well as solvents in the liquid phase process) are in particular chlorobenzene, ortho-dichlorobenzene, para-dichlorobenzene, the isomers of trichlorobenzene, toluene, the isomers of xylene and mixtures of the abovementioned solvents. Step a) may in particular be performed as described in WO 2018/114846 A1, page 19, line 7 to page 25, line 33, wherein gas phase phosgenation (see page 21, line 24 to page 25, line 33 of WO 2018/114846 A1) is particularly preferred.

The phosgenation in step a) is followed by step b) the workup of the obtained liquid crude process product comprising the isocyanate to be produced. The workup of the crude isocyanate may be carried out by well known methods. Examples are described in EP-A-1 413 571, US 2003/0230476 A1 (TDI), and EP 0289 840 B1 (HDI, IDPI and H12-MDI).

Dissolved phosgene and dissolved hydrogen chloride are optionally initially separated from the liquid crude process product obtained in step a) in a separate step b.1). This process mode is preferred especially when the phosgenation in step a) is performed in the liquid phase because the liquid crude process product obtained in a liquid phase phosgenation tends to contain significantly higher proportions of dissolved phosgene and dissolved hydrogen chloride than that obtained in a gas phase phosgenation. Step b.1) may in principle be performed in any manner known to those skilled in the art, in particular by distillation, absorption or a combination of both. Possible embodiment are set out hereinbelow by reference to various variants.

Step b.1) may be followed, or in particular when performing step a) in the gas phase step a) may be immediately followed, by a separation of solvent in a separate step b.2). Step b.2) may be performed in any manner known to those skilled in the art, in particular by distillation. Possible embodiment are set out hereinbelow by reference to various variants.

In Step b.3) of the process according to the invention the isocyanate to be produced is isolated by distillation. This may in principle be done in any manner known to those skilled in the art for this purpose. Possible embodiment are set out hereinbelow by reference to various variants.

Various embodiments are possible for the detailed configuration of the workup according to step b). Preferred variants are specified hereinbelow using the example of TDI:

Variant 1

Variant 1 which is suitable particularly when step a) is performed in the liquid phase is in principle described in Chem System's PERP Report for TDI/MDI (Chem Systems, Process Evaluation Research Planning TDI/MDI 98/99 S8, Tarrytown, N.Y., USA: Chem Systems 1999 pp. 27 to 32). In this variant after distillative separation of hydrogen chloride and phosgene (corresponding to step b.1) in the terminology of the present invention) the liquid reaction mixture still contains, based on its total mass, a solvent proportion of >50% by mass, preferably 51% by mass to 85% by mass, particularly preferably 55% by mass to 65% by mass. This mixture is sent to a solvent separation (corresponding to step b.2) in the terminology of the present invention), wherein initially in a pre-evaporator a solvent-TDI mixture is distilled off in a solvent distillation column. In the solvent distillation column solvent is distilled off and returned to the process. The bottoms stream from this solvent distillation contains, based on the total mass of the bottoms, not only TDI but especially also preferably 15% by mass to 25% by mass of solvent based on the total mass of this bottoms stream. This stream is passed into a so-called intermediate column in which further solvent is distilled off and the bottoms product freed of solvent is sent to a final distillation column for purification of the TDI. Said column is operated at negative pressure and provides the purified saleable isocyanate TDI as a distillate stream (corresponding to step b.3) in the terminology of the present invention). A portion of the TDI remains in the distillation bottoms stream from this final distillation column. The tasks of the intermediate column and the distillation column for TDI purification may also be combined in a dividing wall column as described in US 2003/0230476 A1 to obtain a vaporous stream of low boilers and solvent, a fraction of pure TDI as a distillate stream withdrawn in the region of the dividing wall and a product stream containing TDI and higher-boiling components (distillation residue) as a distillation bottoms stream. The distillation bottoms stream from the distillation column for TDI purification/the dividing wall column combining the intermediate column and TDI purification column is worked up for recovery of TDI. To this end it is possible to pass this stream into the pre-evaporator of the solvent distillation as shown in figure II.A.5 of the cited PERP system report. The bottoms product from this pre-evaporator is then sent to the workup for recovery of TDI present therein. The treatment in the "TDI Residue Processing Facility" shown in figure II.A.6 in Chem System's PERP Report for TDI/MDI (Chem Systems, Process Evaluation Research Planning TDI/MDI 98/99 S8, Tarrytown, N.Y., USA: Chem Systems 1999, pp. 27 to 32) can be replaced by step c) of the present invention. Since in this embodiment the starting material supplied to step c) still contains solvent (namely in particular 2.0% by mass to 10% by mass of solvent based on the total mass of this starting material) as a result of the introduction of the distillation bottoms stream from step b.3) into the pre-evaporator of the solvent separation from step b.2) it is preferable to perform step 1) and separate this solvent therein before the drying in step 2). It is naturally also possible to abstain from introducing the distillation bottoms stream from step b.3) into the pre-evaporator and instead send this distillation bottoms stream directly to the workup in step c).

Variant 2

In contrast to variant 1 in this embodiment after distillative separation of hydrogen chloride and phosgene the liquid reaction mixture still contains a solvent proportion of only ≤50.0% by mass based on its total mass. This mixture is supplied to a pre-evaporator from which a solvent-TDI mixture is distilled off in a distillation column. In this variant the TDI is already freed of solvent in said distillation column and the bottoms stream from this distillation column may therefore be passed into the TDI purification column, this variant thus comprising one less column than variant 1. The TDI purification column is operated at negative pressure and provides the purified saleable isocyanate TDI as a distillate stream. The tasks of the TDI purification column and the distillation column connected upstream thereof may also be combined in a dividing wall column as described in EP 1 413 571 A 1 to obtain a vaporous stream of low boilers and solvent, a fraction of pure TDI as a distillate stream withdrawn in the region of the dividing wall and a product stream containing TDI and higher-boiling components (distillation residue) as a distillation bottoms stream. The distillation bottoms stream from the TDI purification column/the distillation bottoms stream from the dividing wall column combining the TDI purification column and the distillation column connected upstream thereof is worked up for recovery of TDI. In variant 2 too this workup may be performed according to step c) of the present invention. To this end it is possible to pass this stream into the abovementioned pre-evaporator. The bottoms product from this pre-evaporator is then sent to the workup for recovery of TDI present therein. Since in this embodiment the starting material supplied to step c) still contains solvent (namely in particular 2.0% by mass to 10% by mass of solvent based on the total mass of this starting material) as a result of the introduction of the distillation bottoms stream into the pre-evaporator of the solvent separation it is preferable to perform step 1) and separate this solvent therein before the drying in step 2). It is naturally also possible to abstain from introducing the distillation bottoms stream from step b.3) into the pre-evaporator and instead send this distillation bottoms stream directly to the workup in step c).

Variant 3

Variant 3 comprises the distillation sequences described in variants 2 and 1 but without the pre-evaporator mentioned in each case which supplies a liquid bottoms discharge to the work-up according to step c). In this case, the proportion of distillation residue in the described distillation sequences is passed on via the liquid mass flows to the respective final TDI purification column. This process is likewise known in principle (EP 1 717 223 A2). In this case the complete discharging of the distillation residue proceeds via the distillation bottoms stream from the final distillation column (which in the terminology of the present invention is assignable to step b.3). In variant 3 too the workup of this distillation bottoms stream may be performed according to step c) of the present invention.

Variant 4

This variant is especially employed when step a) is performed in the gas phase. Since the liquid crude process product obtained in a gas phase phosgenation contains dissolved phosgene and dissolved hydrogen chloride in relatively (i.e. relative to the liquid phase phosgenation) small amounts, a separate separation of hydrogen chloride and phosgene in step b.1) can be dispensed with. The liquid crude process product is either directly supplied to a solvent separation (corresponding to step b.2)) in which solvent and any dissolved hydrogen chloride and any dissolved phosgene are distillatively separated overhead or—if the solvent proportion is sufficiently low—it is directly supplied to a TDI purification column. In both cases the TDI purification column is preferably in the form of a dividing wall column. Low boilers (i.e. byproducts having a lower boiling point than TDI, any hydrogen chloride still present and any phosgene still present, any solvent and any inert gases) are withdrawn overhead as vapors. The purified TDI is discharged as a distillate stream in the region of the dividing wall. The resulting distillation bottoms stream contains the distillation residue, a certain amount of TDI not distilled off to keep the distillation bottoms stream processable and any traces of solvent. It will be appreciated that two serially arranged distillation columns without a dividing wall may also be employed instead of a dividing wall column.

In this variant the solvent separation according to step b.2)—if performed—is preferably performed at a temperature in the range from 160° C. to 200° C. and at a pressure in the range from 160 mbar to 220 mbar, wherein both reported ranges relate to the bottoms of the employed distillation column. This affords a bottoms stream which, based on its total mass, preferably contains 9% by mass to 20% by mass of solvent, 79% by mass to 90% by mass of TDI and 1% to 5% by mass of compounds having a boiling point higher than that of TDI.

The TDI purification according to step b.3), in particular when performed in a dividing wall column, is preferably performed at a temperature in the range from 160° C. to 200° C. and at a pressure in the range from 50 mbar to 100 mbar, wherein both reported ranges relate to the bottoms of the employed distillation column. This affords a distillation bottoms stream which, based on its total mass, preferably contains 0.00% by mass to 1.00% by mass of solvent, 80.0% by mass to 95.0% by mass of TDI and 4.00% to 20.0% by mass of compounds having a boiling point higher than that of TDI.

Irrespective of the exact configuration of step b) step b.3) affords in all possible process modes (at least) one distillate stream containing a first portion of the isocyanate to be produced and (at least) one distillation bottoms stream containing a second portion of the isocyanate to be produced and distillation residue. Workup of the distillation bottoms stream is provided for in step c) of the process according to the invention. As elucidated in variants 1 and 2 further bottoms streams may also be supplied with the distillation bottoms stream from step b.3).

The distillation bottoms stream consists not only of proportions of the isocyanate to be produced (which are ideally to be fully recovered) but also any solvent proportions from the distillation residue.

It is preferable to initially preconcentrate the distillation bottoms stream, i.e. to already partially separate the isocyanate to be produced by evaporation without causing the remaining liquid stream to solidify, in a step 1). This preconcentration by partial evaporation may in principle be carried out in any evaporator known to those skilled in the art. It is particularly preferable when step 1) is performed in an evaporator selected from the group consisting of thin film evaporators, climbing film evaporators, falling film evaporators, long tube evaporators, helical tube evaporators, forced circulation decompression evaporators and any combination of these apparatuses. Falling film evaporators are particularly preferred. It is also possible to connect a plurality of evaporators in series. The preconcentration according to step 1) is preferably carried out at a temperature in the range from 120° C. to 180° C. and at a pressure in the range from 10 $mbar_{(abs.)}$ to 60 $mbar_{(abs.)}$, particularly preferably at a temperature in the range from 130° C. to 175° C. and at a pressure in the range from 25 $mbar_{(abs.)}$ to 45 $mbar_{(abs.)}$. Step 1) may be performed continuously or discontinuously. The continuous process mode is preferred.

Step 2) comprises then drying the preconcentrated liquid stream depleted in isocyanate to be produced obtained in step 1) or—when not carrying out step 1)—of the distillation bottoms stream obtained in step b.3) in the drying apparatus according to the invention. This drying is preferably performed at a temperature in the range from 150° C. to 500° C. and at a pressure in the range from 20 $mbar_{(abs.)}$ to 200 $mbar_{(abs.)}$, particularly preferably at a temperature in the range from 185° C. to 320° C. and at a pressure in the range from 50 $mbar_{(abs.)}$ to 180 $mbar_{(abs.)}$, very particularly preferably at a temperature in the range from 250° C. to 310° C. and at a pressure in the range from 80 $mbar_{(abs.)}$ to 150 $mbar_{(abs.)}$.

During the drying the isocyanate to be produced is evaporated and liquefied in the condenser, thus very largely recovering isocyanate originally present in the stream to be dried. What remains is a solid which consists virtually exclusively of distillation residue and in any case still contains traces of the isocyanate to be produced (preferably not more than 1.0% by mass of the isocyanate to be produced, particularly preferably not more than 0.1% by mass of the isocyanate to be produced, in each case based on the total mass of the solid generated in step 2). The solid is preferably continuously discharged from the drying apparatus according to the invention.

It will be appreciated that in addition to the particularly preferred use of the drying apparatus according to the invention other possible applications thereof are conceivable and preferred. The present invention therefore further provides for the use of the drying apparatus according to the invention for drying distillation bottoms streams, oil-containing wastes, paint or coatings wastes, sewage sludges, mineral materials contaminated with organic compounds (in particular correspondingly contaminated soil) or coal slurries.

As already discussed in detail hereinabove distillation bottoms streams generated in the production of isocyanates, in particular TDA, are particularly predestined for workup with the apparatus according to the invention. The same applies to the precursor amines, i.e. especially TDA.

However, distillation bottoms streams generated in the refining of crude oil may also be advantageously worked up with the drying apparatus according to the invention.

The following examples illustrate the use of the drying apparatus according to the invention in the workup of TDI. However, it is immediately apparent to a person skilled in the art that the invention is in no way limited thereto.

EXAMPLES

Employed apparatus: Shovel dryer in which the starting material to be dried is applied to a heated bed of mechanically stirred and fluidized granulate material composed of dried starting material (from an earlier drying operation).

The vapor dome of the dryer had been provided with a drainage channel. The vapor conduit of the dryer had been provided at a low point with a drainage funnel.

Heating temperature: 280° C. to 305° C.;
Process pressure: 90 mbar$_{(abs.)}$ to 120 mbar$_{(abs.)}$;
Starting material to be dried: 800 kg/h to 1100 kg/h of a mixture of TDI and high-boiling secondary components (residue) in an approximate mass ratio of 1:1.
Rotor speed: 5 to 42 rpm.

Example 1 (Comparative)

The vapor dome and the vapor conduit were completely insulated (40 mm mineral wool plus applied sheet metal to protect from moisture). The vapor dome including the vapor discharge port were heated via a heating jacket with heat transfer medium having a temperature of 300° C. to prevent condensation.

No TDI drips were apparent via sightglasses installed at the vapor dome and at the vapor conduit. After a run time of 5 days the dryer needed to be shut down due to a differential pressure buildup between the dryer space and the TDI condenser. In a subsequent visual inspection it was determined that the vapor discharge port and the vapor conduit had a massive coating of solid deposits. The entire cross section of the vapor path was blocked in several places. The inner surfaces of the vapor dome were coated with an approximately 10 cm-thick layer of brown solid; the TDI discharge channel had completely disappeared in the solids layer.

Example 2 (Inventive)

The vapor conduit and the vapor dome of the shovel dryer were completely stripped of insulation. The supply to the jacket heating of the vapor dome and the vapor discharge port was stopped.

A continuous flow of TDI was observed via sightglasses installed at the TDI condensate collection points at the vapor dome drainage channel and at the drainage funnel of the vapor conduit. After a run time of 14 days the dryer was switched off and the vapor path visually inspected. It was found that the inner surfaces of the vapor discharge port and the vapor conduit were completely free from solids. With the exception of a very thin black layer the inner surfaces of the vapor dome were free from solid deposits. With the exception of a few granulate particles the TDI drainage channel was completely clean and the drain free. Accordingly the entire vapor path of the dryer was free and said dryer was able to be operated further without any buildup of differential pressure.

The invention claimed is:

1. A drying apparatus configured to perform a drying operation of a starting material to be dried to obtain a dried material and a vapor phase, comprising:
    a dryer comprising a heatable drying space having a feed opening for the starting material, a discharge opening for the dried material and a passage for the vapor phase, wherein the passage opens into a vapor dome comprising a discharge opening for the vapor phase;
    a condenser connected downstream of the discharge opening for the vapor phase; and
    an unheated vapor conduit connecting the discharge opening for the vapor phase with the condenser;
    wherein
    (i) the vapor dome, but not the unheated vapor conduit, is configured so that partial condensation of the vapor phase occurs in the vapor dome, but not in the unheated vapor conduit, during the drying operation, or
    (ii) the unheated vapor conduit, but not the vapor dome, is configured so that partial condensation of the vapor phase occurs in the unheated vapor conduit, but not in the vapor dome, during the drying operation, or
    (iii) the vapor dome and the unheated vapor conduit are configured so that partial condensation of the vapor phase occurs in the vapor dome and the unheated vapor conduit during the drying operation,
    wherein a drainage means for constituents of the vapor phase liquefied in the partial condensation is arranged:
    (1) inside the vapor dome in the case where the vapor dome, but not the unheated vapor conduit is configured so that partial condensation of the vapor phase occurs in the vapor dome, but not in the unheated vapor conduit, or
    (2) inside the unheated vapor conduit in the case where the unheated vapor conduit, but not the vapor dome is configured so that partial condensation of the vapor phase occurs in the unheated vapor conduit, but not in the vapor dome, or
    (3) inside the vapor dome and inside the unheated vapor conduit in the case where the vapor dome and the unheated vapor conduit are configured so that partial condensation of the vapor phase occurs in the vapor dome and the unheated vapor conduit, and
    wherein the drainage means is configured such that the constituents liquefied in the partial condensation are discharged via a discharge opening (i) from the vapor dome, or (ii) from the unheated vapor conduit, or (iii) from the vapor dome and from the unheated vapor conduit, thereby separating the liquefied constituents from constituents of the vapor phase not liquefied in the partial condensation.

2. The drying apparatus as claimed in claim 1, wherein the dryer comprises a product-turning vacuum dryer having a horizontal screw, a rotary dryer, a disc dryer, a belt dryer, or a granulating screw.

3. The drying apparatus as claimed in claim 2, wherein the dryer comprises a product-turning vacuum dryer comprising kneader dryer, a paddle dryer.

4. The drying apparatus as claimed in claim 1, wherein the partial condensation of the vapor phase is realized (a) by not having insulation of the vapor dome and/or of the unheated vapor conduit, or (b) by not having a system to heat the vapor dome and/or the unheated vapor conduit, or (c) by a means for cooling the vapor dome and/or the unheated vapor conduit, or (d) by a combination of two or more of the abovementioned measures.

5. The drying apparatus as claimed in claim 1, wherein the vapor dome comprises a drainage means selected from the group consisting of drainage channels connected to a drainage conduit and droplet collectors connected to a drainage conduit.

6. The drying apparatus as claimed in claim 1, wherein the unheated vapor conduit comprises a drainage means selected from the group consisting of a drainage funnel connected to a drainage conduit, low points in the unheated vapor conduit connected to a drainage conduit, and drainage channels in the unheated vapor conduit connected to a drainage conduit.

7. The drying apparatus as claimed in claim 1, wherein the condenser is selected from the group consisting of a tube bundle heat exchanger, a plate heat exchanger and a spray condenser.

8. A process for producing an isocyanate by phosgenation of the primary amine corresponding to the isocyanate to be produced to obtain a liquid crude process product comprising the isocyanate to be produced, comprising the distillative workup of the liquid crude process product to obtain a distillation bottoms stream;

wherein the process further comprises workup of the distillation bottoms stream, wherein the workup comprises:

1) optional preconcentration of the distillation bottoms stream in an evaporator by partial evaporation of the isocyanate to be produced present in the distillation bottoms stream, wherein a preconcentrated liquid stream depleted in isocyanate to be produced is obtained;

2) drying the distillation bottoms stream or the preconcentrated liquid stream depleted in isocyanate to be produced obtained in step 1) in a drying apparatus as claimed in claim 1, wherein, while forming a solid process product as dried material, isocyanate to be produced is obtained as a vapor phase and liquefied in the condenser.

9. The process as claimed in claim 8, wherein the phosgenation is performed in the liquid phase in the presence of a solvent.

10. The process as claimed in claim 8, wherein the phosgenation is performed in the gas phase to generate a gaseous process product containing the isocyanate to be produced, wherein the gaseous process product is cooled by contacting with a quenching liquid selected from the group consisting of solvent, the isocyanate to be produced and mixtures of the isocyanate to be produced and solvent, thereby providing the liquid crude process product comprising the isocyanate to be produced.

11. The process as claimed in claim 8, wherein the drying in step 2) is performed at a temperature in the range from 150° C. to 500° C. and at a pressure in the range from 20 $mbar_{(abs.)}$ to 200 $mbar_{(abs.)}$.

12. The process as claimed in claim 8, comprising step 1), wherein the preconcentration is performed at a temperature in the range from 120° C. to 180° C. and at a pressure in the range from 10 $mbar_{(abs.)}$ to 60 $mbar_{(abs.)}$.

13. A process of drying a starting material, comprising drying the starting material with the drying apparatus of claim 1 to obtain a dried material and a vapor phase, wherein the starting material is selected from the group consisting of a distillation bottoms stream, an oil-containing waste, a paint or coatings waste, a sewage sludge, a coal slurry, and a mineral material contaminated with organic compounds.

14. The process as claimed in claim 13 comprising drying distillation bottoms streams, wherein the distillation bottoms streams are generated (a) in the production of isocyanates, or (b) in the production of primary amines which may be converted into isocyanates, or (c) in the refining of crude oil.

* * * * *